United States Patent [19]

Wakamori et al.

[11] 3,962,457

[45] June 8, 1976

[54] METHODS OF KILLING MITES USING S-β-NAPHTHYLMETHYL-N,N-DIMETHYL-THIOLCARBAMATE

[75] Inventors: Shigeki Wakamori, Shimizu; Haruki Ogawa, Fujieda; Masayoshi Yamaguchi; Seigo Kanamori, both of Shimizu, all of Japan

[73] Assignee: Kumiai Chemical Industry Co., Ltd., Tokyo, Japan

[22] Filed: Jan. 24, 1975

[21] Appl. No.: 543,774

[30] Foreign Application Priority Data

Jan. 21, 1974 Japan.................................. 49-8548

[52] U.S. Cl................................ 424/300; 424/303; 424/308; 424/330; 424/340

[51] Int. Cl.$^2$......................................... A01N 9/20
[58] Field of Search..................................... 424/300

[56] References Cited
FOREIGN PATENTS OR APPLICATIONS 7,304,525   2/1973   Japan

*Primary Examiner*—Jerome D. Goldberg
*Assistant Examiner*—Allen J. Robinson
*Attorney, Agent, or Firm*—Oblon, Fisher, Spivak, McClelland & Maier

[57] ABSTRACT

Parasitic mites are eliminated from plants by a method which comprises applying an effective amount of S-β-naphthylmethyl-N,N-dimethylthiolcarbamate to said plants.

3 Claims, No Drawings

METHODS OF KILLING MITES USING S-β-NAPHTHYLMETHYL-N,N-DIMETHYLTHIOLCARBAMATE

BACKGROUND OF THE INVENTION

1. Field of the Invention

The present invention relates to a miticide.

2. Description of Prior Art

Fruit trees, industrial crops, vegetbles and ornamental plants, such as citrus fruit, apple, pear, tea, cotton, Japanese cedar trees, eggplant, cucumber, strawberry, rose, carnation, chrysanthemum, etc., in the past have been known to be damaged by mites. Control of mites has been difficult. The lifetime of each generation of mites is usually about 20 days. One generation of mites will produce as many as 10 or more generations each year. In order to control each generation, therefore, it becomes necessary to apply the miticides repeatedly. The difficulty with repeated applications, however, is that due to the rapid regeneration of the mites, the mites tend to develop a resistance to the repeatedly applied miticides, which build-up of resistance seems to be developed more rapidly than the build-up of resistance of many other insects to insecticides.

The development period of mites involves successive growth stages starting from the ovum, extending to larva, and finally reaching the formation of adults capable of reproduction.

Thus, it would be most desirable to provide a miticide which will act simultaneously as adulticides, larvicides, ovicides, and which additionally maintain their effect over a long period of time.

In the present invention, S-β-naphthylmethyl-N,N-dimethylthiolcarbamate has been found to possess miticidal characteristics which are quite different from conventional miticides. This compound, however, is not novel per se. Japanese Pat. Publication No. 4525/1973 discloses that this compound has been used as a herbicide, but it has not heretofore been disclosed as possessing any miticidal characteristics.

SUMMARY OF THE INVENTION

Accordingly, it is one object of the present invention to provide a miticide which possesses the characteristics of an adulticide, a larvicide, and an ovicide and which maintains its effect over a long period of time.

This and other objects of this invention, as will hereinafter be made clear by the discussion below, have been attained by providing a miticide which comprises S-β-naphthylmethyl-N,N-dimethylthiolcarbamate. The miticide of the invention is preferably a combination of S-β-naphthylmethyl-N N-dimethylthiolcarbamate, and one or more compounds selected from the group consisting of ethyl-O-Benzoyl-3-chloro-2, 6-dimethoxybenzohydroximate, isopropyl-4,4'-dibromobenzilate, 4-chloro-3-n-propylthiophenyl-4-nitrophenyl ether, 4-chloro-3-n-propylsulfinylphenyl-4-nitrophenyl ether and 1,5-di-(2,4-dimethylphenyl)-3-methyl-1,3,5-triazapenta-1,4-diene.

DETAILED DESCRIPTION OF PREFERRED EMBODIMENTS

The inventors have examined various S-naphthylmethyl-thiolcarbamates derivatives and have found that S-β-naphthylmethyl-N,N-dimethylthiolcarbamate has an excellent miticidal effect as compared to analogous compounds. The ovicidal effect of the miticide of this invention is quite remarkable. This miticide also has imagocidal and larvacidal effects. Accordingly, even when the miticide is applied during the development period of mites, the mites can be controlled for long periods. Consequently, the required number of applications of this miticide is low when compared to the requirements for the conventional compositions, whereby the requisite labor and cost for control is decreased. Furthermore, the development of resistance by the mites to the miticide is delayed.

The miticide of the invention is effective against sensitive mites as well as mites which are resistant to organic compounds such as 2,2,2-trichloro-1,1-di-(4-chlorophenyl)ethanol (hereinafter referred to as TCDCPE); and 2,4,4,5-tetrachlorodiphenyl sulphone hereinafter referred to as TCDPS). Mites which can be controlled by applying the miticide of this invention include those which are parasites on plants such as Panonychus citri (citrus red mite), Panonychus ulmi (European red mite). Tetranychus Urticae (two-spotted spider mite), Tetranychus telarius (carmine mite), Tetranychus Kanzawai (Kanzawa spider mite), Oligonychus hondoensis and Bryobia Practiosa (clover mite), etc; or on animals such as Boophilus microphlus, Haemaphysalis bispinosa, Argas persicus, etc. The miticide is especially effective against mites which are parasitic on citrus fruit and apple trees.

The miticide of the invention can be combined with other miticides, insecticides, fungicides, germicides, herbicides, or fertilizers. The active ingredient of the miticide of this invention, S-δ-naphthylmethyl-N,N-dimethyl thiolcarbamate is a yellow transparent viscous liquid having a boiling point of 148°–153°C at 10.02 mmHg and a refractive index, $n_D^{20}=1.6343$.

It is preferred to use the compound of this invention with one or more additional compounds selected from the group consisting of ethyl-O-benzoyl-3-chloro-2,6-dimethoxybenzohydroximate, isopropyl-4,4'-dibromobenzilate, 4-chloro-3-n-propylthiophenyl-4-nitrophenyl ether, 4-chloro-3-n-propylsulfinylphenyl-4-nitrophenyl ether and 1,5-di-(2,4-dimethylphenyl)-3-methyl-1,3,5-triazapenta-1,4-diene. When the additional compound is combined, the following advantages are derived:

1. The required dose of total active ingredients is lower than that of a single active ingredient because of synergistic effects. Also, the effective period for controlling the mites is prolonged. Accordingly, the attendant cost and labor is decreased and the onset of resistance to the miticide is delayed.

2. The effectiveness of this combination against mites which are resistive to the organic compounds, TCDCPE and TCDPS, is quite high.

3. The effectiveness of this combination against mites which are hard to control by a single miticide is quite high. Accordingly, the spectrum of the kinds of mites which can be controlled is broadened.

The total amount of the active ingredient which need be applied to stems and leaves is 0.1 to 3,000 ppm, preferably 25 – 500 ppm. This amount and the manner of application will not result in killing the plant, and hence the miticidal application here is quite different from the herbicidal applications of the prior art. The weight ratio of the added compound to S-β-naphthylmethyl-N,N-dimethylthiolcarbamate is 0.1 – 3.0, preferably 0.3–1.0. The total amount of the active ingredient applied to a field should be 50 – 1000 g per 10 acre.

The active ingredient may be formulated by combination with various additives such as diluents, e.g., talc, kaolin, silicon dioxide, diatomaceous earth; solvents, e.g., xylene, toluene, acetone, cyclohexane; surfactants, e.g., sodium ligninsulfonate, polyoxyethylene alkylaryl ether, etc.

Having generally described the invention, a more complete understanding can be obtained by reference to certain specific examples, which are included for purposes of illustration only and are not intended to be limiting unless otherwise specified. In the examples, S-β-naphthylmethyl-N,N-dimethylthiolcarbamate is referred to as NMDT and the terms "percent" and "part" indicate percent by weight and part by weight.

EXAMPLE 1

Emulsion

A mixture was prepared by uniformly mixing 50 parts of NMDT, 35 parts of xylene, and 15 parts of "Sorpol" (1) (a mixture of polyoxyethylene nonylphenyl ether and calcium dodecylbenzene sulfonate). The mixture was diluted with water before application.

EXAMPLE 2

Wettable powder

A wettable powder was prepared by mixing and crushing 20 parts of NMDT, 35 parts of diatomaceous earth, 35 parts of talc, 5 parts of silicon dioxide and 5 parts of Sorpol (2) (a mixture of polyoxyethylene nonylphenyl ether and sodium dodecylbenzene sulfonate). The wettable powder is dispersed in water before application.

EXAMPLE 3

Powder

A powder was prepared by mixing and crushing 3 parts of NMDT, 47 parts of talc, 47 parts of clay and 3 parts of silicon dioxide.

EXAMPLE 4

Emulsion

A mixture was prepared by mixing 30 parts of NMDT, 15 parts of O-benzoyl-3-chloro-2,6-dimethoxybenzohydroximate, 45 parts of xylene and 15 parts of Sorpol (1). The mixture is diluted with water before application.

EXAMPLE 5

Emulsion

A mixture was prepared by mixing 30 parts of NMDT, 20 parts of isopropyl-4,4'-dibromobenzilate, 35 parts of xylene and 15 parts of Sorpol (1). The mixture is diluted with water before application.

EXAMPLE 6

Wettable powder

A wettable powder was prepared by mixing and crushing 20 parts of NMDT, 10 parts of 4-chloro-3-n-propylthiophenyl-4-nitrophenyl ether, 30 parts of diatomaceous earth, 30 parts of talc, 5 parts of silicon dioxide and 5 parts of Sorpol (2). The wettable powder is dispersed in water before application.

EXAMPLE 7

Wettable powder

A wettable powder was prepared by mixing and crushing 20 parts of NMDT, 10 parts of 4-chloro-3-n-propylsulfinylphenyl-4-nitrophenyl ether, 30 parts of diatomaceous earth, 30 parts of talc, 5 parts of silicon dioxide and 5 parts of Sorpol (2). The wettable powder is dispersed in water before application.

EXAMPLE 8

Wettable powder

Wettable powder was prepared by mixing and crushing 20 parts of NMDT, 10 parts of 1,5-di-(2,4-dimethylphenyl)-3-methyl-1,3,5-triazapenta-1,4-diene, 30 parts of diatomaceous earth, 30 parts of talc, 5 parts of silicon dioxide and 5 parts of Sorpol (2). The wettable powder is dispersed in water before application.

Certain experiments demonstrating the biological effects of the miticides of the invention will be described.

EXPERIMENT 1

Test of Ovumcidal effect on Panonychus citri (Citrus red mite)

In unglazed pots having diameters of 15 cm, two-year-old orange trees (Chinese citron) were planted. 50 g of Citrus red mite adults were inoculated so as to blow 50 – 100 ova. After blowing, the adults were removed. The emulsion prepared by the above-mentioned formula (1), was diluted and was sprayed at a dose of 30 ml per pot. The compounds shown in Table 1 were used as a reference. The mortality rate of the ova (ovumcidal rate) was observed 10 days after the spraying treatment. The results are shown in Table 1.

Table 1

| Active ingredient | Mortality rate (%) | | | | | Phytoxicity |
|---|---|---|---|---|---|---|
| | 200 ppm | 100 ppm | 50 ppm | 25 ppm | 12.5 ppm | |
| NMDT | 100 | 100 | 100 | 100 | 92.7 | None |
| TCDCPE | 100 | 100 | 87.2 | 42.1 | 16.7 | " |
| Carbamate Ⓐ | 85 | 67 | 31 | 6 | 0 | " |
| Carbamate Ⓑ | 81 | 53 | 15 | 0 | 0 | " |
| Non-treatment | 0 | 0 | 0 | 0 | 0 | " |

Carbamate Ⓐ : S-(4-chlorobenzyl) N,N-dimethylthiol carbamate
Carbamate Ⓑ : S-(2-chlorobenzyl) N,N-dimethylthiol carbamate

EXPERIMENT 2

Test on Panonychus citri (Citrus red mite) adults which are resistive to organic phosphorus compounds In unglazed pots having diameters of 15 cm. young orange tree plants were placed. 100 Citrus red mite adults were inoculated. The emulsion prepared by the above-mentioned formula (1) was diluted to 500 ppm, and was sprayed at a dose of 30 ml per pot. The compounds listed in Table 2 were used as a reference. Living adult counts were taken after 5, 15, 25 and 35 days. The results are shown in Table 2.

Table 2

| Active ingredient | Living-adult counts | | | | Phytoxicity |
|---|---|---|---|---|---|
| | 5 days | 15 days | 25 days | 35 days | |
| NMDT | 0 | 0 | 0 | 0 | None |
| (Dithioate A) | 47 | 90 | 125 | 147 | " |
| Carbamate Ⓐ | 0 | 3 | 25 | 123 | " |
| Carbamate Ⓑ | 0 | 2 | 73 | 151 | " |
| Non-treatment | 109 | 124 | 176 | 243 | " |

(Dithioate A): S-(2,5-dichlorophenylthiomethyl)0,0-diethylphosphorodithioate

EXPERIMENT 3

Test on Panonychus Ulmi (European red mite) adults

In unglazed pots having diameters of 15 cm, young apple tree plants were placed. 100 European red mite adults were inoculated. The emulsion prepared by the above-mentioned formula (1) was diluted to 500 ppm and was sprayed at a dose of 30 ml per pot. Living adult counts were taken after 3, 10, 20, 30 and 40 days. The results are shown in Table 3.

Table 3

| Active ingredient | Living-adult counts | | | | | Phytoxicity |
|---|---|---|---|---|---|---|
| | 3 days | 10 days | 20 days | 30 days | 40 days | |
| NMDT | 0 | 1 | 0 | 0 | 3 | None |
| Non-treatment | 116 | 127 | 186 | 252 | 236 | None |

EXPERIMENT 4

Test on Tetranychus Urticae (two-spotted spider mite)

In unglazed pots having diameters of 15 cm, young apple tree plants were placed. 50 two-spotted spider mite adults were inoculated and the pots were placed in a greenhouse. The emulsion prepared by the above-mentioned formula (4) was diluted and was sprayed at a dose of 30 ml per pot. The living-adult counts were observed after 3, 10, 20, 30 and 40 days. The results are shown in Table 4. No phytoxicity was found. The active ingredients used are as follows:

NMDT  
Benzomate: ethyl-0-benzoyl-3-chloro-2,6-dimethoxybenzohydroximate  
Phenysobromolate: isopropyl-4,4'-dibromobenzilate  
CPTN: 4-chloro-3-n-propylthiophenyl-4-nitrophenyl ether  
CPSN: 4-chloro-3-n-propylsulfinylphenyl-4-nitrophenyl ether  
DMTD: 1,5-di-(2,4-dimethylphenyl)-3-methyl-1,3,5-triazapenta-1,4-diene.

Table 4

| Active ingredient | Concentration (ppm) (I) + (II) | Living adult counts | | | | |
|---|---|---|---|---|---|---|
| | | 3 days | 10 days | 20 days | 30 days | 40 days |
| NMDT (I) + Benzomate (II) | 100 + 60 | 0 | 0 | 0 | 2 | 4 |
| | 50 + 30 | 1 | 0 | 2 | 4 | 7 |
| | 25 + 15 | 3 | 2 | 4 | 7 | 16 |
| NMDT (I) + Phenysobromolate | 100 + 60 | 0 | 0 | 0 | 0 | 2 |
| | 50 + 30 | 1 | 0 | 2 | 2 | 5 |
| | 25 + 15 | 3 | 1 | 3 | 5 | 11 |
| NMDT (I) + CPTN (II) | 100 + 60 | 0 | 1 | 3 | 5 | 8 |
| | 50 + 30 | 2 | 1 | 3 | 7 | 10 |
| | 25 + 15 | 4 | 5 | 7 | 9 | 16 |
| NMDT (I) + CPSN (II) | 100 + 60 | 0 | 0 | 1 | 3 | 5 |
| | 50 + 30 | 1 | 2 | 4 | 7 | 12 |
| | 25 + 15 | 5 | 3 | 5 | 11 | 20 |
| NMDT (I) + DMTD (II) | 100 + 60 | 0 | 0 | 0 | 5 | 7 |
| | 50 + 30 | 2 | 2 | 4 | 7 | 11 |
| | 25 + 15 | 5 | 4 | 6 | 9 | 15 |
| NMDT | 200 | 3 | 0 | 4 | 9 | 21 |
| | 100 | 6 | 4 | 12 | 22 | 34 |
| | 50 | 16 | 21 | 30 | 43 | 54 |
| Benzomate | 120 | 8 | 10 | 15 | 26 | 37 |
| | 60 | 13 | 18 | 26 | 34 | 52 |
| | 30 | 24 | 27 | 39 | 51 | 67 |
| Phenysobromolate | 120 | 4 | 1 | 9 | 14 | 20 |
| | 60 | 8 | 5 | 13 | 20 | 32 |
| | 30 | 13 | 21 | 32 | 40 | 56 |
| CPTN | 120 | 14 | 16 | 21 | 32 | 47 |
| | 60 | 18 | 23 | 32 | 40 | 68 |
| | 30 | 28 | 34 | 42 | 54 | 75 |
| CPSN | 120 | 12 | 15 | 23 | 30 | 42 |
| | 60 | 16 | 24 | 35 | 42 | 59 |
| | 30 | 22 | 29 | 37 | 46 | 68 |
| DMTD | 120 | 20 | 31 | 47 | 53 | 62 |
| | 60 | 24 | 35 | 52 | 64 | 75 |
| | 30 | 30 | 36 | 59 | 68 | 82 |
| Non-treatment | 0 | | 46 | 63 | 78 | 92 | 114 |

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. A method of killing parasitic mites on plants which comprises applying to said mites a miticidally effective amount of S-$\beta$-naphthylmethyl-N,N-dimethyl thiolcarbamate.

2. The method of claim 1, wherein the mites are Panonychus citri.

3. The method of claim 1, wherein said compound is applied in an amount of from 0.1 to 3000 ppm.

* * * * *